United States Patent
Santiago et al.

(10) Patent No.: US 8,311,373 B1
(45) Date of Patent: Nov. 13, 2012

(54) CAPILLARY ELECTROPHORESIS CHEMICAL SENSOR

(75) Inventors: Francisco Santiago, Fredericksburg, VA (US); Alfredo N. Rayms-Keller, Fredericksburg, VA (US); Victor H. Gehman, Jr., Dahlgren, VA (US); Karen J. Long, Upper Marlboro, MD (US); Kevin A. Boulais, Waldorf, MD (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 668 days.

(21) Appl. No.: 12/462,062

(22) Filed: Jul. 22, 2009

(51) Int. Cl.
G02B 6/00 (2006.01)
G01N 21/00 (2006.01)

(52) U.S. Cl. .......................... 385/12; 356/337
(58) Field of Classification Search ............... 385/12
See application file for complete search history.

(56) References Cited

U.S. PATENT DOCUMENTS

| | | | |
|---|---|---|---|
| 6,444,133 B1 | 9/2002 | Fajardo et al. | 216/24 |
| 6,597,851 B2 | 7/2003 | Johnson et al. | 385/131 |
| 7,016,584 B2 | 3/2006 | Lee et al. | 385/125 |
| 7,058,242 B2 | 6/2006 | Lidorikis et al. | 385/11 |
| 7,082,242 B2 * | 7/2006 | Fajardo et al. | 385/127 |
| 7,151,629 B2 | 12/2006 | Takagi et al. | 359/321 |
| 7,305,164 B2 * | 12/2007 | Williams et al. | 385/123 |
| 2005/0169590 A1 * | 8/2005 | Alkeskjold | 385/123 |

FOREIGN PATENT DOCUMENTS
WO WO 2004/090510 10/2004

OTHER PUBLICATIONS

Michael L. Korwin-Pawlowski ; Ewa Dabek-Zlotorzynska ; Wojtek J. Bock; Application of photonic band gap fibers in capillary electrophoresis systems. Proc. SPIE 5952, Optical Fibers: Applications, 59520E (Oct. 4, 2005); doi:10.1117/12.622293, online, retrieved on Sep. 5, 2012 from url: http://spiedigitallibrary.org/.*
Francisco Santiago et al., Technical Proposal "Effects of Liquid and Gaseous Defects to Optical Properties of Photonic Band-gap Structures", W911NF-06-R-0005, Jun. 19, 2006.

* cited by examiner

*Primary Examiner* — Omar Rojas
(74) *Attorney, Agent, or Firm* — Gerhard W. Thielman, Esq

(57) ABSTRACT

A detector is provided for sampling and identifying a material, such as a medium in which the detector is disposed. The detector includes an annular photonic crystal fiber, first and second electrodes, an electrical power supply, an illumination source and an analyzer. The fiber has opposite longitudinal ends, surrounds a center core tube and includes fused capillary tubes. The electrodes are disposed between the fiber's longitudinal ends. The electrical power supply connects between the electrodes. The illumination source emits light into the core tube from one of the opposite ends. The analyzer for compares an emission pattern from light transverse to the fiber against an established pattern, and indicates match in response to correspondence between the patterns. The annular structure has a two-dimensional optical photonic bandgap. The analyzer monitors the emission pattern by optical frequency domain reflectometry or optical time domain reflectometry.

8 Claims, 11 Drawing Sheets

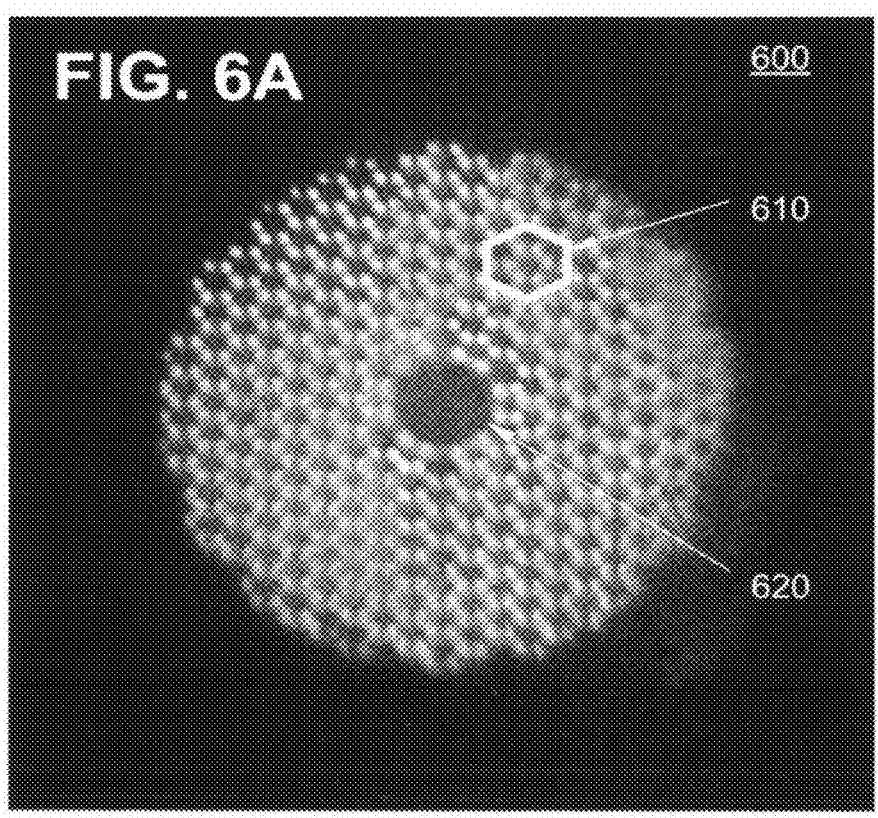
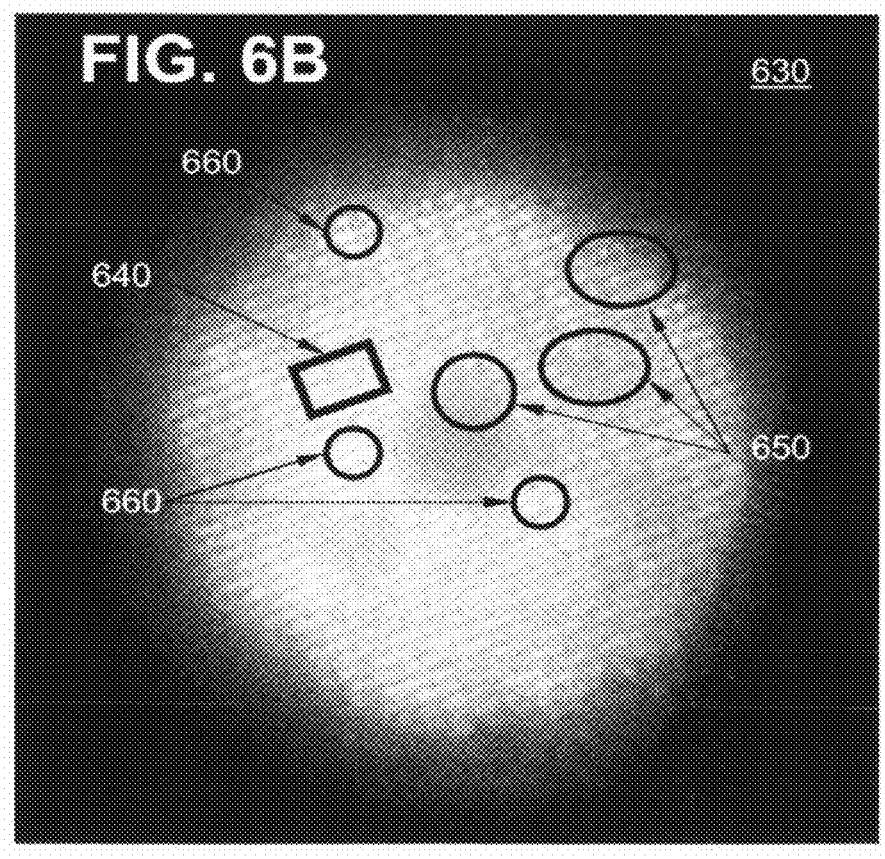

Contour Map of Transverse Index Profile at Z=0 ically identified known exemplary embodiments of the present invention, particularly related to convenience and sensitivity.

CAPILLARY ELECTROPHORESIS CHEMICAL SENSOR

STATEMENT OF GOVERNMENT INTEREST

The invention described was made in the performance of official duties by one or more employees of the Department of the Navy, and thus, the invention herein may be manufactured, used or licensed by or for the Government of the United States of America for governmental purposes without the payment of any royalties thereon or therefor.

BACKGROUND

The invention relates generally to chemical sensors. In particular, relates to chemical sensors that employ an annular photonic crystal fiber coupled to an illumination source at one end to transmit an emission pattern transverse to the fiber's outer surface for comparison against an established pattern to detect the presence of a signature material.

The United States faces various technical challenges to national security, including threats from chemical and biological warfare (CBW) agents, as well as detection of toxic industrial chemical (TIC) materials. Depending on the technology used, conventional CBW detectors are capable of identifying and/or detecting between eight and twenty different agents, with verification and validation of field results usually requiring approximately forty-eight hours. The most accurate identification of about twenty chemicals including most chemical warfare agents and some volatile organic compound (VOC) molecules is conventionally performed, in the field and in the laboratory, by gas-chronomatography-mass-spectrometry (GCMS).

Both commercial enterprises and military organizations desire a detector capable of identifying known and novel CBW and TIC agents to defend both war-fighters and civilians. Some CBW agents are very deadly to large numbers of people. For example in 1984, exposure to concentrations of forty metric tons of methyl-isocyanate over an area of several hundred square miles in Bhopal, India in 1984, killed about thirty-eight-hundred people with economic loss of several hundred million dollars.

SUMMARY

Conventional detection techniques yield disadvantages addressed by various exemplary embodiments of the present invention, particularly related to convenience and sensitivity. In particular, various exemplary embodiments provide a detector that enhances the reliability and timeliness for detection of chemical and biological agents by modifying the confinement properties of the waveguide due to changes in the photonic band gap, thereby contrasting from more conventional sensing mechanism that uses optical absorption. This technique enables light to escape and form a pattern at the surface of the photonic crystal fiber to be compared to a pattern database as the main information discriminator.

These exemplary embodiments provide a detector for sampling and identifying a material, such as a medium in which the detector is disposed. The detector includes an annular photonic crystal fiber, first and second electrodes, an electrical power supply, an illumination source and an analyzer.

The fiber has opposite longitudinal ends, surrounds a center core tube and includes fused capillary tubes. The electrodes are disposed between the fiber's longitudinal ends. The electrical power supply connects between the electrodes. The illumination source emits light into the core tube from one of the opposite ends. The analyzer for compares an emission pattern from light transverse to the fiber against an established pattern, and indicates match in response to correspondence between the patterns.

In various exemplary embodiments, the annular structure has a two-dimensional optical photonic band-gap. In alternate embodiments, the analyzer monitors the emission pattern by optical frequency domain reflectometry or optical time domain reflectometry.

BRIEF DESCRIPTION OF THE DRAWINGS

These and various other features and aspects of various exemplary embodiments will be readily understood with reference to the following detailed description taken in conjunction with the accompanying drawings, in which like or similar numbers are used throughout, and in which:

FIG. 6A is an optical micrograph showing light propagating through the fiber;

FIG. 6B is a an optical micrograph of the fiber after exposure to liquid methanol;

DETAILED DESCRIPTION

Figure 1A:
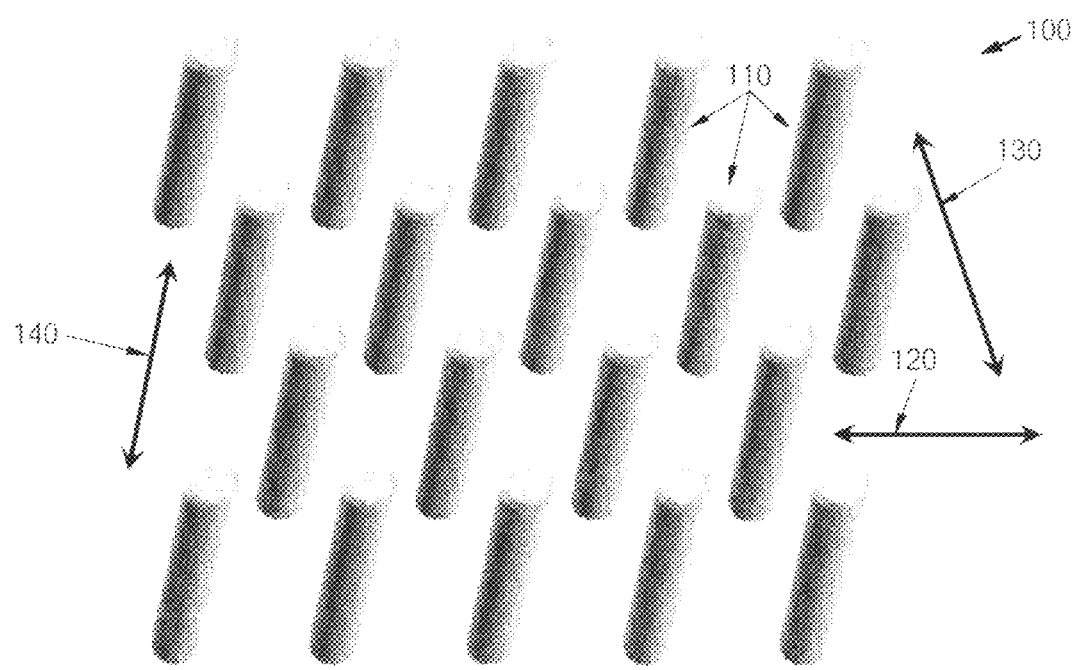
FIG. 1A is an isometric view of a periodic array of suspended glass rods.

In the following detailed description of exemplary embodiments of the invention, reference is made to the accompanying drawings that form a part hereof, and in which is shown by way of illustration specific exemplary embodiments in which the invention may be practiced. These embodiments are described in sufficient detail to enable those skilled in the art to practice the invention. Other embodiments may be utilized, and logical, mechanical, and other changes may be made without departing from the spirit or scope of the present invention. The following detailed description is, therefore, not to be taken in a limiting sense, and the scope of the present invention is defined only by the appended claims.

Various exemplary embodiments employ the modification of the confinement properties of the waveguide due to changes in the photonic band gap, rather than optical absorption, as the primary sensing mechanism. This modification enables light to escape and form a pattern at the surface of the fiber. The pattern formed at the surface of the photonic crystal fiber is used as the main information discriminator. Effects caused by defects on light propagation can be evaluated through two-dimensional optical photonic band-gap (2DPB) structures in the presence or absence of chemical vapors and or chemical aerosols. Such information can be used to develop miniature sensors based on 2DPB capable of performing multiple measurements of several properties of a specimen in the same instance of observation using minimum space, energy, and consumables.

Various exemplary embodiments enhance the reliability and timeliness for detection of chemical and biological agents. This can be accomplished by implementation of photonic crystal fibers as a multifunctional chemical detector capable of concurrently measuring several properties of one sample during observation that minimize space, energy, and consumables. Further, sensors made from 2DPB technology can be used to supplement more conventional detection technologies to minimize false positive readings. Photonic crystal technology enables such evaluation, and various exemplary embodiments integrate the instrumentation into a robust system, such as on a single semiconductor chip.

Despite accurate and rapid analysis provided by GCMS, such conventional systems present portability constraints due to the weight of the portable detectors with a minimum of eighty pounds, and by their high-rate power consumption that limits batteries to only a few, hours of operation. Even with GCMS detectors, a single detector cannot identify most of the important TIC materials of military concern. The limitation is further complicated regarding detection of both novel chemical and/or biological agents.

Most current detection technologies work by careful detection and characterization of one or two physical properties on each observation of a sample, thereby introducing the comparison of cost and risk. For example, in circumstances under which a high-risk situation must be avoided, more resources are necessary for detection and identification with sensors capable of detecting very small amounts of agents having very low rates of false positive readings.

Unfortunately, compromises between sensitivity, accuracy and detection time are needed with the conventionally available technologies. A system capable of measuring and characterizing many physical properties of a sample in a short observation period mitigates many of the compromises faced conventionally. For example, a multi-agent fast detector with higher probability of false positive readings might be better suited for operational requirements than a fast detector with low probability of false positive detections for a particular agent. Further, an array of several sensors, each optimized to a different agent, could be implemented as a super-sensitive multi-agent detection system. Advances in microelectronics, microfluidics and micro-electro-mechanical systems (MEMS), with their inherent ability for systems integration, may provide an efficient toolbox to overcome the current challenges.

Various exemplary embodiments provide an optical device known as photonic crystal fiber as a microscopic laboratory in which several optical, electrical and mechanical properties can be performed on the same sample in the same observation instance. Due to their small size and enhanced properties, these new fibers could be used in micro-mechanical, microfluidics and microelectronics environments. Photonic crystal fibers are composed from a center-core capillary tube surrounded by an ordered array of capillary tubes. The ordered array forms a two-dimensional cross-sectional lattice.

Thus, various exemplary embodiments provide a system to perform measurements of many physical properties of a sample in one observation time interval. This enables flexibility for integrating many specialized sensor systems in a small portable and low-maintenance package. Further, fiber waveguide components such as fiber gratings, laser fibers, polarization maintaining fibers and splitters enable optical and electro-optical package integration.

This special ordering brings a periodic fluctuation of optical refractive index between the optical index of the glass and the constructive or destructive interference pattern when photons at a particular wavelength attempt to penetrate the periodic structure. For optimal destructive interference conditions, an optical "band gap" develops in the lattice. The term optical band gap is borrowed from the solid-state terminology of electronic band gap that applies to the electrical properties of semiconductors.

A photonic band-gap structure (PBS) represents a periodic arrangement of elements with different dielectric constants. Such structures may include two-dimensional periodic arrays of glass rods in air, capillary tubes or three-dimensional arrangements of spheres in space. FIG. 1A shows an isometric view 100 of a periodic array of suspended glass rods 110, which are arranged along alignment lines 120, 130 and 140. The elements of the array may consist of any two materials provided these have differing dielectric constants.

The physics that describes these systems is scale-invariant. This means that PBS can be constructed to interact with electromagnetic waves from all parts of the spectrum. Structures with dimensions of centimeters interact with microwaves; structures with dimensions of micrometers interact with light; and structures of dimensions of nanometers interact with x-rays. These photonic band-gap structures are special in their manner of interaction with the electromagnetic waves. These applications emphasize the visible portion of the electromagnetic spectrum.

Figure 1B:
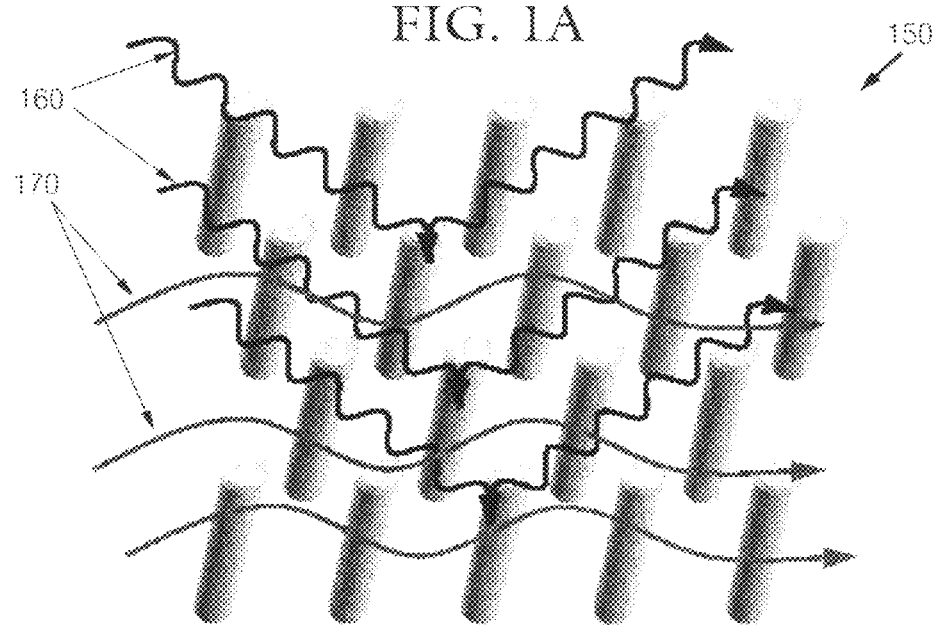
FIG. 1B is an isometric view of a periodic array of dielectrics interacting with light of two colors—black is light with interfering wavelength and gray light with non-interfering.

The periodic arrangement of the dielectric elements creates an environment where the reflections of light waves by the dielectric elements interfere either constructively or destructively. However, only light waves of particular wavelength can interfere with the structure. The proper wavelength is determined by the fundamental periodic distance between the elements. FIG. 1B shows an isometric view 150 of a periodic array of dielectrics as rods 110 interacting with light of two colors or wavelengths. The dark short-wavelength rays 160 represent light that interferes, and the lighter long-wavelength rays 170 represent light that is non-interfering.

The time independent electromagnetic equations (Maxwell's equations) of the periodic boundary conditions found in photonic band-gaps are analogous to the quantum mechanical wave equation (Schrödinger's equation) that describes the trajectories of electrons traveling through a crystalline medium. The solutions of both equations are almost identical. In PBS, the periodic dielectric constant assumes the rôle of the quantum potential of the wave equation.

Figure 2:
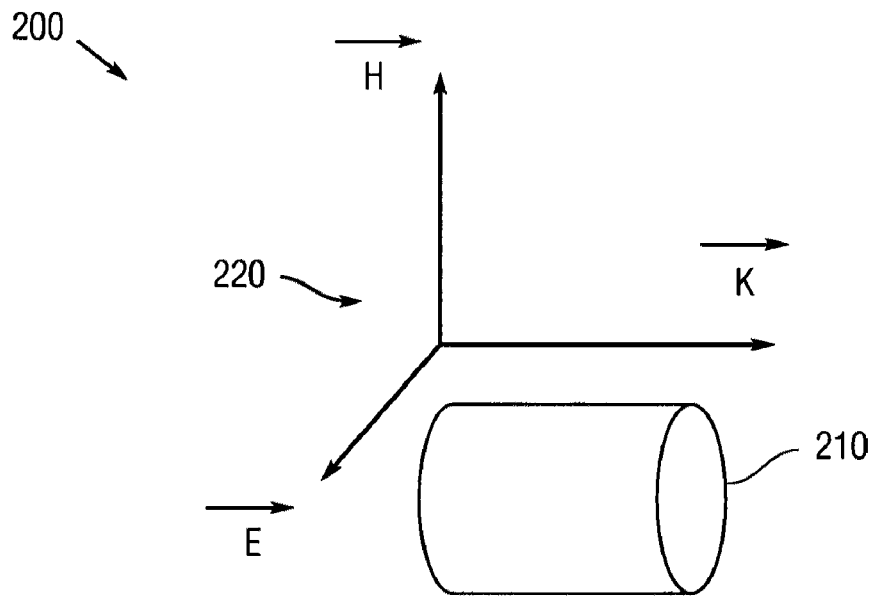
FIG. 2 is an isometric view of a geometry of relative orientation of the vectors K, E and H with respect to light propagation along a cylinder.

FIG. 2 illustrates an isometric view 200 of the medium 210 (as a cylinder) and a compass rose 220 with axes for the orthogonal vectors associated with these quantities. The vectors include $\vec{k}$ as the light propagation vector (through the medium 210), $E(\vec{r})$ as the electric field (along the cylinder's radius) and H as the magnetic field, being perpendicular to the other two vectors.

Figure 3:
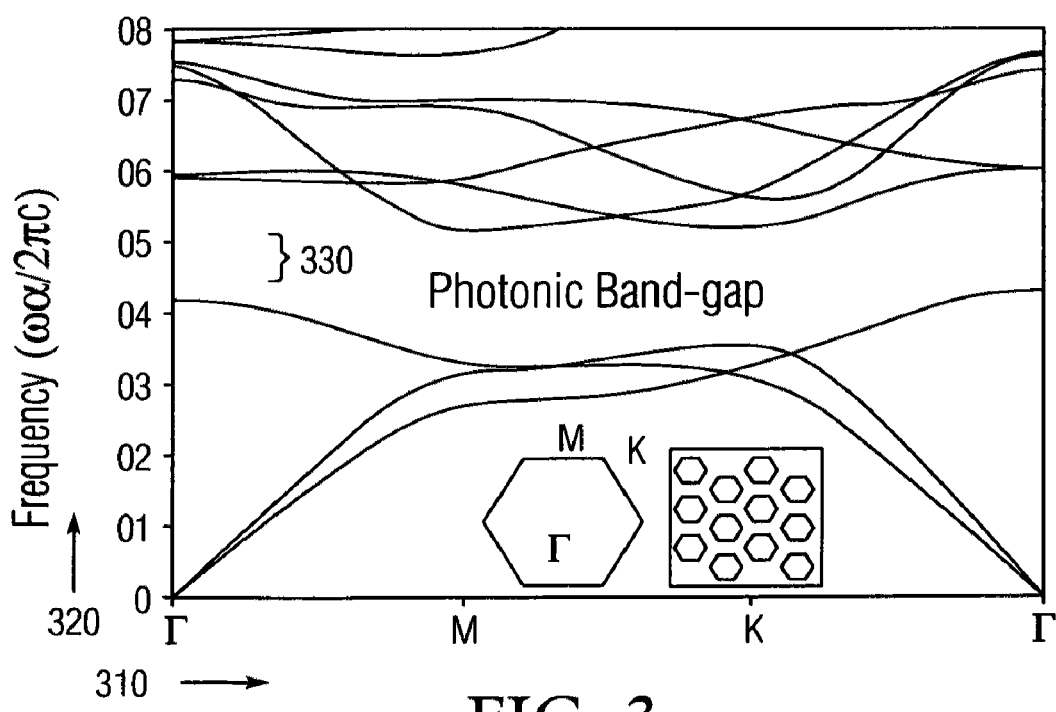
FIG. 3 is a graphical view of a plot showing relationship between light wavelength and ability to travel in different directions inside the plane of the array.

FIG. 3 provides a graph 300 showing the relationship between light wavelength and ability to travel in different directions inside the plane of the array. The graph 300 includes an abscissa 310 of light direction and an ordinate 320 of frequency. A photonic band gap appears between upper and lower sets of curves about half-way along the ordinate corresponding to green light wavelengths.

Figure 4A:
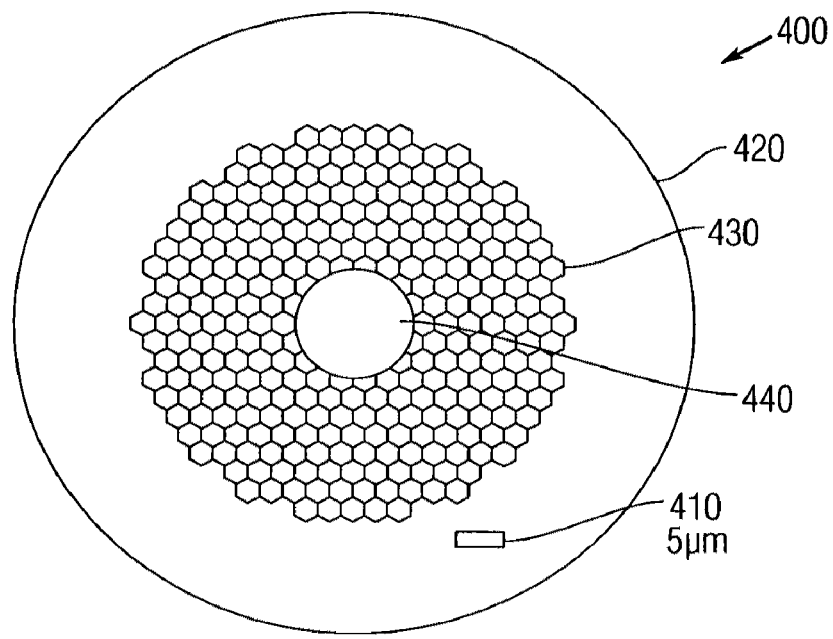
FIG. 4A is a scanning electron micrograph of a photonic fiber using a 2 DBG, with total diameter of the micrograph as 30 micrometers.

FIG. 4A shows a scanning electron micrograph (SEM) 400 of the cross section of a photonic crystal fiber that uses a 2DPB array of fused capillary tubes superimposed with a (5μ) scale 410. The total diameter of the fiber is twenty micrometers (or 20μ denoted as microns). The fiber includes an outer sheath 420, an annular array of tubes 430 in hexagonal pattern, and a center tube 440. The tubes are composed of glass to confine or "guide" light traveling perpendicular to the page. The center tube 440 has a diameter of ten microns. The smaller annular tubes 430 surrounding the center tube 440 represent the primary component of the photonic crystal. The annular tubes 430 are fused to form the continuous wall of a honeycomb array. This illustrated fiber is designed as an optical waveguide for telecommunication applications. This example represents only one of the many configurations and applications of the techniques described herein or envisionable therefrom.

Figure 4B:
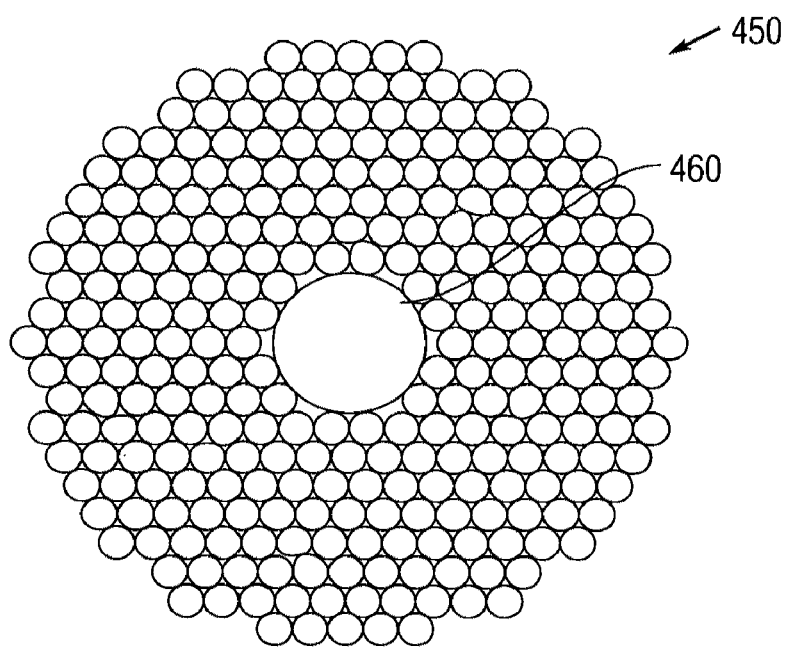
FIG. 4B is a scanning electron micrograph of a confining green light to center core of the fiber.

To become a photonic crystal, the honeycomb must have a particular periodic symmetry. The annular tubes 430 can be fused in a square, rectangular, or triangular array. A closer inspection of the SEM 400 reveals that the honeycomb walls are not without defects. FIG. 4B illustrates another SEM 450 of the identical photonic fiber in the SEM 400 under an alternate application of confining green light to the center core 460 of the fiber.

Some of the tubes 430 are not completely circular, and there are deviations of the periodic pattern. These types of defects affect the photonic properties of the fiber. Because these defects originate predominantly from the manufacturing process, they vary between fibers produced from different lots. The implementation of a sensor includes a procedure to "subtract" the defects analogous to a background subtraction or baseline definition to a signal. However, typically the defects in commercially available fiber can be neglected.

The vector quantities can be expressed by relations for Periodic Potential Quantum Mechanics:

$$-\frac{\hbar^2}{2m}\nabla_E^2 \Psi(\vec{r}) + V(\vec{r})\Psi_E(\vec{r}) = E\Psi_E(\vec{r}), \quad (1)$$

where h is the Dirac constant (equaling the Plank constant h divided by $2\pi$), m is an integer, $\Delta^2_E$ is the del vector differential operator for kinetic energy (represented by the nabla symbol), $\Psi_E$ is the probability density factor, $\vec{r}$ is the position vector, E is energy, and with the periodic potential V expressed as:

$$V(\vec{r}+m\vec{G})=V(\vec{r}), \quad (2)$$

where $\vec{G}$ is cyclic period representing a vector of periodic properties of the PBS. Other solutions may be obtained by translation by crystal momentum vector $\tilde{K}$ related to $\vec{G}$ or by rotation and translation of that vector, which is obtained by Fourier transform of $\vec{G}$.

In addition, Electromagnetism Periodic Dielectrics can be expressed by the following relation:

$$\Psi_E(\vec{r},t)=\Sigma_K c_E \Psi_E(\vec{r})e^{iEt/\hbar}, \quad (3)$$

where t is time, $C_E$ is the electric Fourier coefficient, $i=\sqrt{-1}$, and summation is over the entire electromagnetic field, and with the Periodic Potential Periodic Dielectric Solution expressed as:

$$\nabla \times \frac{1}{\varepsilon(\vec{r})}\nabla \times H_\omega(\vec{r}) = \frac{\omega^2}{c^2}H_\omega(\vec{r}), \quad (4)$$

where $\Delta\times$ is the curl differential operator, c is dielectric value, $H_\omega$ is periodic magnetic field, $\omega$ is frequency, and electromagnetism periodic dielectrics can be expressed as:

$$\in(\vec{r}+m\vec{G})\in(\vec{r}), \quad (5)$$

which leads to the solution:

$$H_\omega(\vec{r},t)=\Sigma_\omega c_\omega H_\omega(\vec{r})e^{\omega t}, \quad (8)$$

where $c_\omega$ is the magnetic Fourier coefficient. The magnetic field H has a periodic condition expressed as:

$$H(\vec{r},t)=H(\vec{r}+m\vec{G},t) \quad (7)$$

due to the periodic nature of the solution that restricts propagation through the PBS to only harmonic modes.

The magnetic field H is restricted by being transverse to the propagation vector $\vec{k}$ along the main axis of the medium 210, as well as to the electric field $E(\vec{r})$ along the radius of the cylinder representing the medium 210. The periodic nature of the solution for the PBS imposes limits on the types of solutions available. For example, only harmonic modes can propagate through the PBS. Also, in some particular directions and values of the propagation vector $\vec{k}$, the harmonic modes cannot propagate. This means there are mathematical solutions to the periodic dielectric that do not physically exist, i.e., there are frequency values of $\omega$ where the solution to the equation cannot exist. These values form a continuous exclusive region known as the band-gap.

Another consequence of the periodicity includes many redundancies in the solutions. However, not all the solutions for every $\vec{k}$ are necessary. Instead, only select values of $\vec{k}$ lead to all other solutions determinable by either a translation by the vector $\tilde{K}$ related to $\vec{G}$, or by a rotation and a translation by the vector $\tilde{K}$.

Figure 5:
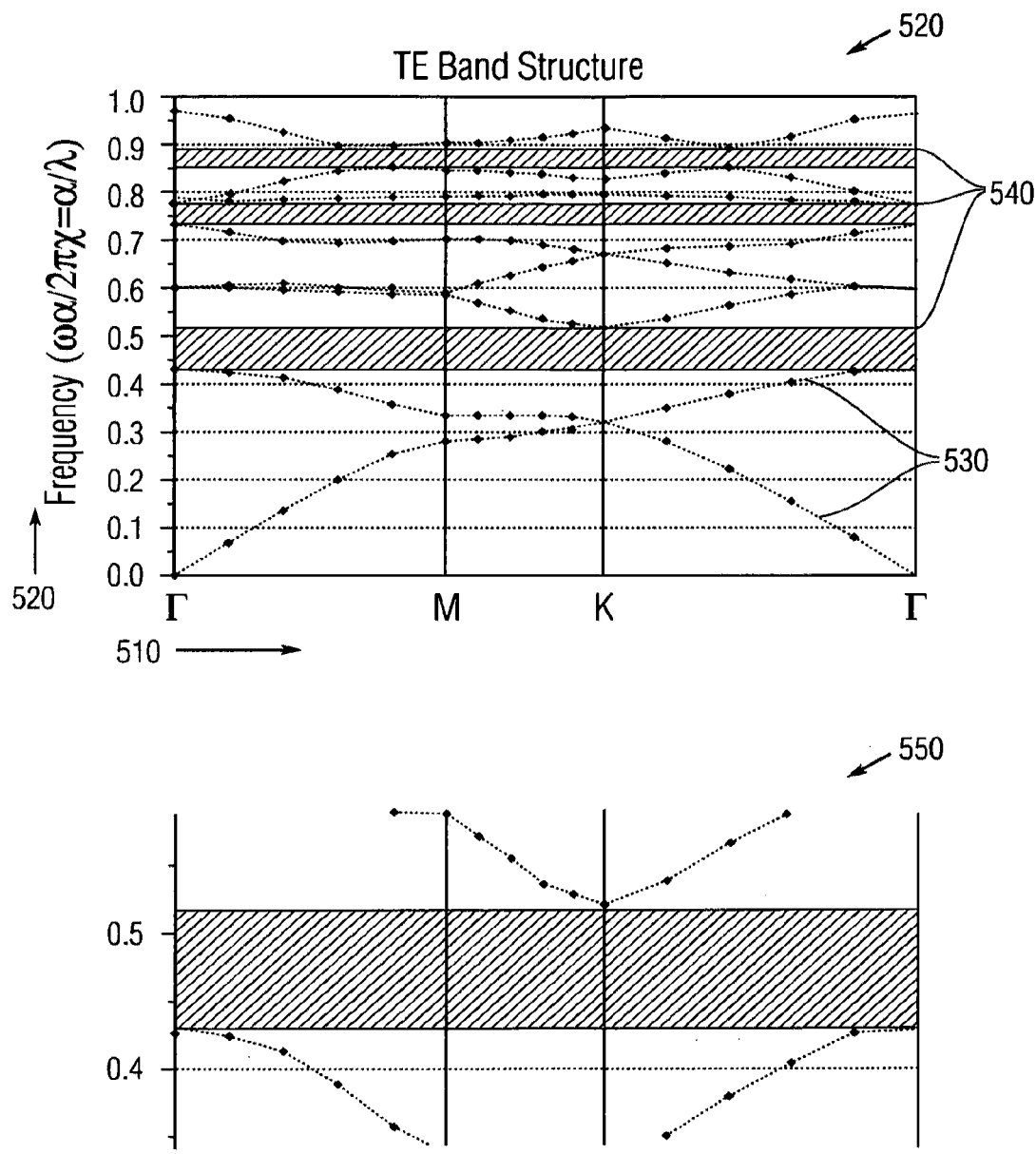
FIG. 5 is a graphical view of a modes plot of a 2DPB showing band-gap—top and bottom—close-up of the band-gap region.

FIG. 5 represents a graph 500 showing the frequencies of the allowed modes for a typical PBS as a function of $\vec{k}$ vectors that form the Brillouin zone. The abscissa 510 represents the $\vec{k}$ light propagation vector, and the ordinate 520 represents the frequency $\omega$. Allowed modes are denoted by diamonds plotted along curves 530. The dash-bands 540 across the graph 500 indicate the band-gaps, with one example shown in detail 550. The values of $\vec{k}$ required to generate all of the solutions form what is known as the Brillouin zone.

Band-gaps 540 are displayed as the plot of the magnitude and direction of $\vec{k}$ that form the Brillouin zone in the axial direction and the frequency of the allowed modes in the transverse direction. In addition, most of the allowed modes are displayed simultaneously in the graph 500. Generally the modes intersect but sometimes do not, such as conditions in which the values of frequency ω are not allowed. The difference between the highest value of one mode with the lowest value of the next higher mode is the value of the band-gap. Light of a frequency in the band-gap does not travel through the PBS. Because the band-gap parameters are controlled by the PBS geometry, PBS can be designed to produce a particular band-gap of interest.

For an imperfect periodic structure however, some frequencies that are should be part of the band-gap may be able to propagate through the PBS. Imperfections of the periodic structure can be caused by the termination or truncation of the periodicity as in the surface (surface states) or by anomalies inside the periodic structure. In the case of PBS, a region with a dielectric constant different from another region creating the period can produce such states. The defects produced by an external chemical substance (gas or liquid) can be studied to determine their effects on the properties of PBS towards detection and identification of the presence of the substance.

Because the properties of light inside a PBS are analogous to the properties of an electron inside a crystal, much of the knowledge from theoretical solid-state physics in the last half-century applies to the study of photonic band-gap structures. Solid-state physics includes considerable study in the effects of imperfections or defects of the periodic structure to the transport properties of electrons traveling inside the crystal. In addition, there is a very large body of knowledge addressing the effects of the periodic structure termination (surface states) to the properties of the electrons traveling inside a crystal.

FIG. 6A shows an optical micrograph 600 of a similar 2DPB array fiber to the SEM 400 in FIG. 4A. In this example, the opposite end of the fiber is illuminated with broadband white light. This is an example of a typical system to be studied for follow-on materials properties measurement and analysis. The optical micrograph 600 illustrates an ordered array of both bright and dark spots in a hexagonal arrangement 610. In addition, the spots surrounding the center tube 620 appear with greater intensity and incidentally feature a shift in color toward red. Further, the spots towards the outer diameter feature a shift in color toward blue.

The change of the spot intensity patterns at both inner and outer diameters are examples of the defects created by the truncation of the periodic structure at both ends (surface states). Finally, a closer examination at the spots inside the array denotes several anomalous features. These features are examples of imperfections or defects of the periodic structure. For a given periodic arrangement, the visual map of spots is very dependent on the ratio of the dielectric constants between the mediums of glass and air. For glass channels from the capillary tubes to be filled with a gas or liquid having a different dielectric constant than air, the spot pattern undergoes a drastic change. In some cases, the array pattern may completely disappear.

FIG. 6B shows a micrograph 630 illustrating the same fiber of FIG. 6A, in which the fiber is exposed to a drop of liquid methanol. Considerable non-specular scattered light is particularly noticeable, appearing almost out-of-focus. In addition, the light pattern in exposed micrograph 630 has changed from the initial micrograph 600. One can observe the absence of the hexagonal dark spots, and additionally the bright spots are smaller and their pattern changed from hexagonal 610 to rectangular 640. Further, darker sectors 650 with reddish colors appear in contrast to lighter sectors 660. In this example, the methanol drop is drawn in by capillary force and the amount inside the capillaries varies between neighboring capillaries. Other materials with different dielectric constant affect the regular pattern and surface states in alternate ways. These changes can be used to identify the gas or liquid filling the channels.

Another detection approach is to design an array that displays a particular spot pattern or "resonate" when the channels are filled with a substance of interest. For example, the fiber can be tailored to display a sharp pattern 610 when exposed to a particular concentration of methanol or any other chemical substance of interest. Further, because the optical properties are associated with the periodicity of the array, a much larger sized periodic array can be constructed, thereby enabling the hosting of a biological agent. The larger structure could then be tuned to a higher harmonic to "resonate" with the fluorescence of a bio-agent exposed to ultraviolet light.

This technology can be used for the detection not only of chemical agents and toxic industrial chemicals and for the detection of odors (to determine human presence), illicit narcotics, and unauthorized explosives. Furthermore, this technology may assist monitoring the state of munitions, missiles, and other critical military systems by detecting the presence of decay byproducts.

Figure 7:
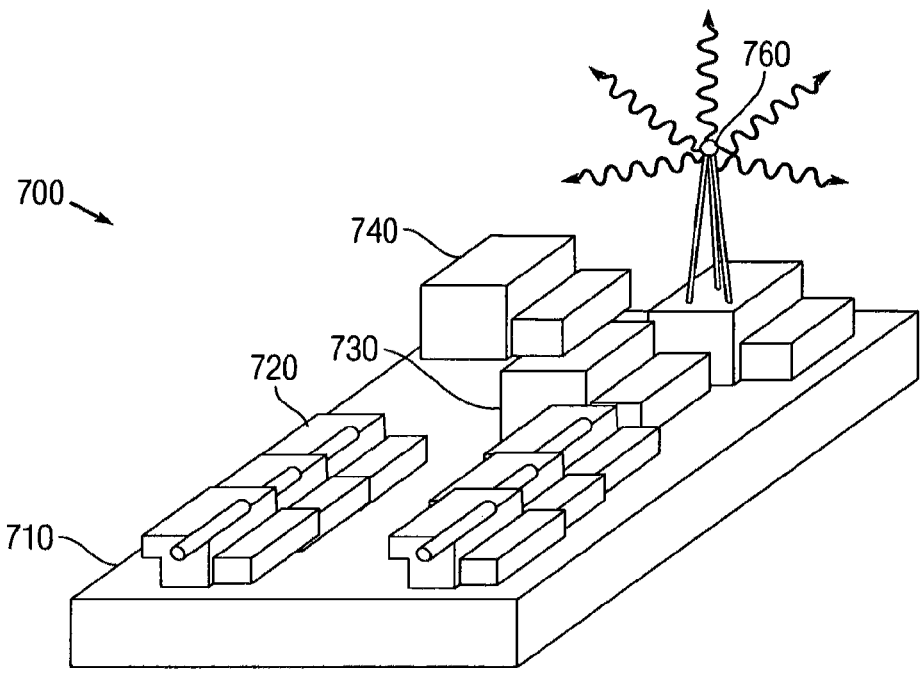
FIG. 7 is a perspective view of a 2DPB micromodule system.

One of the many possible implementations of this technology includes producing reusable miniature detection module. FIG. 7 shows an isometric block diagram 700 of the concept. A multipurpose host card 710 provides a substrate platform for the components disposed thereon. Among these are at least one miniature module (micromodule) 720, power supply 730, microfluidic support 740, and transmitter 750 with antenna 760. To achieve this, 2DPB technology can be integrated with microelectromechanical systems (MEMS) technology.

Each micromodule 720 can be integrated in a battlefield configurable network supported by the host card 710 with dimensions of a few square inches that contain the necessary components to provide power, communications, microfluidic, and any other support to the micromodules 720. In addition, the host card 710 enables the micromodules 720 to be interconnected so the specimen (gas or liquid) travels through them. Modules measuring different properties of the specimen of interest could be connected in either serial or parallel configurations to maximize the number of attributes or properties observed.

Exemplary embodiments are intended to provide the warfighter the ability to configure the modules as needed in the theater of operations in a rapid and efficient manner. For example, for a situation requiring minimal false positive readings several micromodules designed to "resonate" at the presence of particular agents of interest could be connected in series. For circumstances requiring reliable ultra-rapid detection, the micromodules could be connected in parallel combination. In addition, 2DPB modules could be integrated with more conventional detection techniques.

Implementing such revolutionary technology involves resolution of some technical issues. For example, in the micrograph 630 of FIG. 6B, in addition to the drastic change of the bright and dark spots, there are distinction of regions, e.g., 650 and 660, due to variations in the volume fraction of methanol between neighboring capillaries. These translate into a difference in net dielectric constant due to different fractional volumes between air and methanol. The 2DPB is sensitive to the ratio of the dielectric constant of glass and the net dielectric constant of whatever fills the capillaries. One particular complication results from there being several ways the gases and/or liquids can mix.

Figure 8:
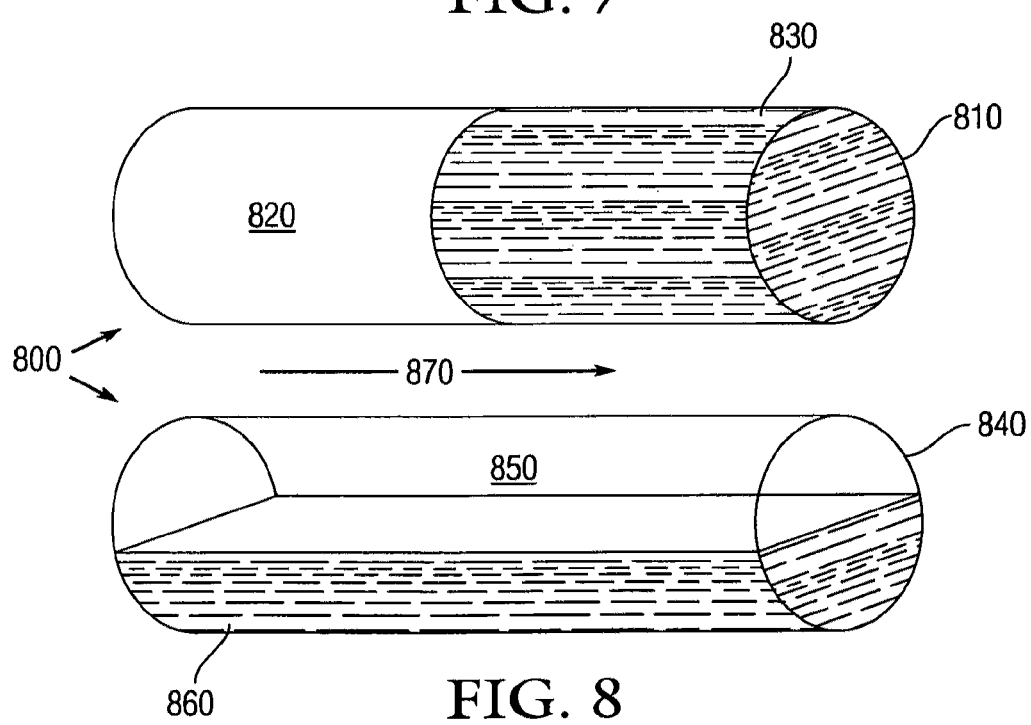
FIG. 8 is an isometric view of chemical mixing as separated inside capillaries.

FIG. 8 shows two simplistic arrangements 800 of mixture between a pair of substances. A first fiber 810 shows axial separation between air 820 (left) and methanol 830 (right). A second fiber 840 shows transverse separation 840 between air 850 (top) and methanol 860 (bottom). Each of these geometries represents extremes in the behavior of the net dielectric constant. The axially separated fiber 810 corresponds to maximum screening relative to the electric field. The transverse separated fiber 820 represents no screening. Most situations lie between these extremes.

In maximum screening for the axial separation fiber 810, the effective dielectric constant ∈ corresponds to:

$$\in = f_a \in_a + f_b \in_b, \quad (8)$$

which $f_a$ and $f_b$ are the respective volume fractions of materials a and b and $\in_a$ and $\in_b$ are their respective dielectric constants. For no screening, the effective dielectric constant ∈ corresponds to:

$$\varepsilon = \left(\frac{f_a}{\varepsilon_a} + \frac{f_b}{\varepsilon_b}\right)^{-1}. \quad (9)$$

For example, for a methanol volume fraction of 0.04 mixed with 0.96 of air volume fraction, using the dielectric constant of methanol at room temperature (20° C.) of 1.75827 yields an effective dielectric of 1.03033 at full screening and an effective dielectric constant of 1.01755 at no screening. The difference above greatly influences the optical properties of the 2DPB. Further, ionic separation in electrolytic solutions has been observed to be confined to cavities of two-hundred-fifty nanometers (250 nm or 0.25µ) in diameter.

Figure 9A:
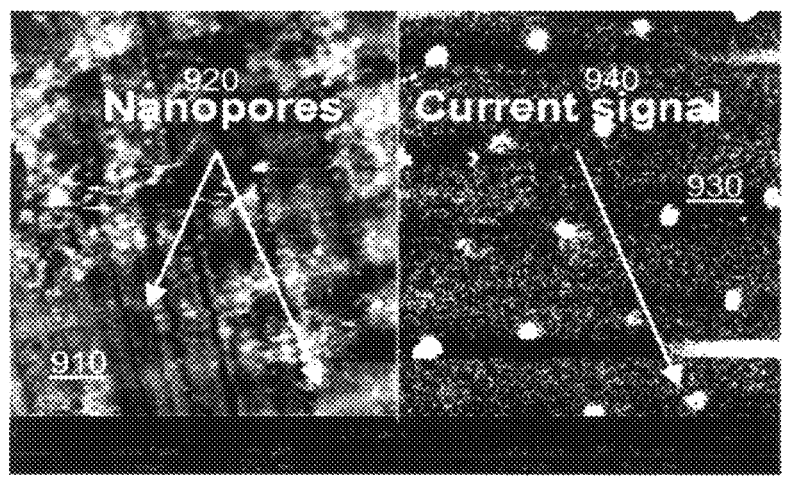
FIGS. 9A and 9B are respectively micrograph maps of electrolytic-filled nanocavities by atomic force microscopy, and a detail view showing current intensity profile across a nanochannel.

FIG. 9A shows simultaneous topographical and current image maps 900 of electrolytic filled nanocavities from conductive atomic force microscopy at comparable scales. On the left is the topographical map 910 with nanocavities 920. On the right is the current signal map 930 with high-current areas 940 denoted as bright dots. The images offer evidence of ionic accumulation next to the walls of the nanocavities. The high current areas 940 appear larger than the size of the corresponding cavities 920.

Figure 9B:
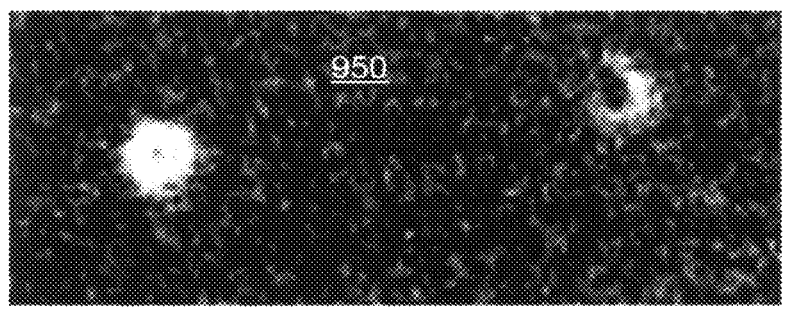
Figure 10:
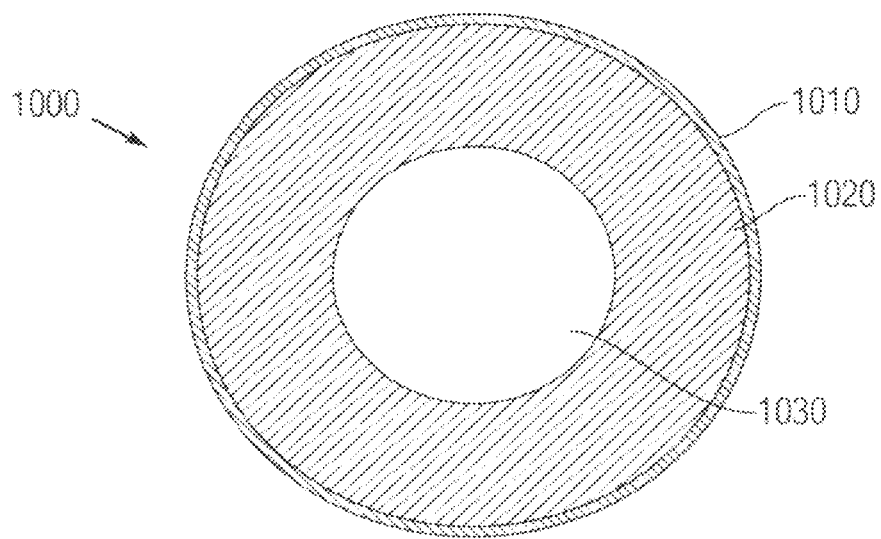
FIG. 10 is an elevation view of concentric dielectric separation.

FIG. 9B presents a detail enlargement 950 of the current map 930 showing a current profile across the cavity 920 from white (higher current) adjacent the wall to gray (lower current) in the center of the cavity 920. The net ionic concentration adjacent the wall is one-thousand times larger than the ionic concentration of the solution. FIG. 10 shows a fiber 1000 in cross-section with an outer rim or sheath 1010, an annular region 1020 containing substance a and a center core region 1030 with substance b. This models methanol along the outer rim 1000 forming an annulus around the air, as indicated in the enlargement 950.

Similarly, gases or liquids with different dipole strengths could separate from a homogeneous mixture and form concentric layers from the wall of the capillaries, with each layer having a different dielectric constant. The dielectric distribution inside the capillaries can be investigated using controlled mixtures prior to determining the effects of chemical substances regarding the optical properties of the 2DPB structure. This can be used to predict dielectric behavior and determine their change to the optical properties of 2DPB for developing techniques for detection, identification, and quantification of a foreign chemical substance of interest.

Upon characterizing the periodic optical properties, a wealth of information can be obtained by selective destruction of the photonic band-gap by introducing material inside the periodic capillaries. The intruding material can be the chemical/biological agent to be detected by the system. The change in optical index of refraction due to the displacement of the interior air creates additional possible paths for the light to traverse the plane of the periodic array and exit the fiber for detection by various techniques. In addition, the photonic fiber can be monitored for "lossy" behavior as the periodic capillaries are filled with the material to be analyzed. The intruding material can be liquid, gas, colloidal particles suspended in liquid or colloidal particulates suspended in gas. In addition to the optical probe, the intruding material can be analyzed electrically by performing measurements like dipole relaxation analysis and by spectroscopic measurements.

Photonic crystal fibers can be employed as a micro-laboratory in which to measure several physical properties of a sample concurrently. The sample can be liquid, gas, colloidal suspension in liquid, or colloidal suspension in gas. Upon introduction of the sample inside the periodic capillary array, several optical, spectroscopic and electrical properties of the sample are measured. Upon completion of the observation interval, information obtained from numerous nearly simultaneous measurements can be compared to perform a positive identification of the sample. For the injection of gas inside the periodic capillary array, various exemplary embodiments employ capillary electrophoresis.

Capillary electrophoresis (CE) provides an analytical technique to separate and identify molecules in liquids to identify biological threat agents. The principle behind CE involves an external electric field to separate the molecules of interest by charge. Positive and negatively charged molecules separate in opposite directions inside an electric field. The molecules of interest are dissolved in a buffer solution optimized to flow past the applied electric field by the mechanism known as electro-osmosis. Upon injection of the molecules of interest and the buffer solution inside a capillary tube, the charges move according to their relative charges inside the applied electric field. At the opposite end of the injection an optical absorption sensor monitors the changes in optical transmission due to the passing of the charge separated molecules.

The optical sensor information can be plotted as a function of the time elapsed for the moment the electric field is applied until the change in optical transmission. This plot may be used to calculate a quantity known as the number of theoretical plates or "N", which is related to the molecule of interest. CE represents very popular technique for studying proteins, and pharmaceuticals. Several variations of CE complement the information obtained by CE. However, if the ability to do spectroscopy in situ with CE were available, a great deal more information can be made available in real-time that enhance the ability of CE to identify unknowns.

Before 2 DBP technology can be realized in such applications, several technical issues require resolution, such as the fundamental interactions between liquids and gases from pre-selected organic solvents introduced inside selected elements of a 2DPB structure evaluated in a controlled methodology. Initially, spectroscopic ellipsometry can be used to determine the dielectric properties of pre-selected liquids and gases in the immediate vicinity of glass surfaces inside extremely small confined structures. These results can be used to prepare special defects to the periodicity of 2DPB using the spectroscopic ellipsometry results from pre-selected liquids and gases to establish the net effect manifests in the optical modes of the 2DPB. Ellipsometry represents an optical technique for investigating dielectric properties (e.g., refractive index) of thin films using elliptical polarization.

Further, a computer model can be developed based on the results of this effort to predict the optical modes in response to a known 2DPB exposed to arbitrary liquid or gaseous chemical compounds. This technology could be used for the detection not only of chemical agents and TIC compounds but also for the detection of human presence (odor), illegal narcotics, and explosives from their VOC release. Moreover, sensors made from 2DPB technology can be used to supplement more conventional detection technologies to minimize false positive readings.

Figure 11:
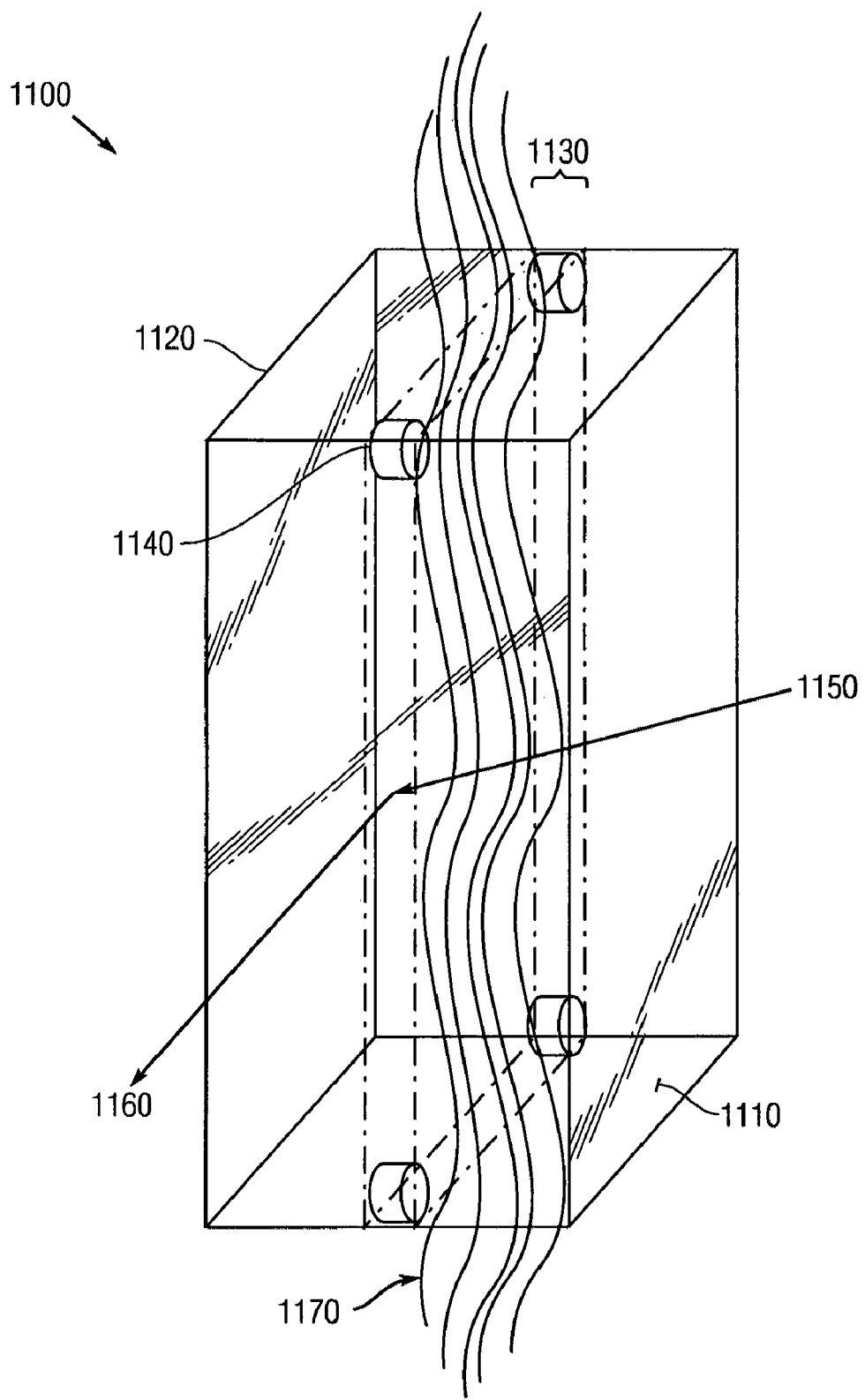
FIG. 11 is an isometric view of a cell for testing dielectric properties of gas and liquids in a confined space.

Dielectric properties of liquid and gases confined in small spaces can be measured by using spectroscopic ellipsometry. FIG. 11 shows an isometric diagram 1100 of such a cell. Such a cell for the study can include a pair of parallel glass plates: right plate 1110 and left plate 1120 separated by a gap 1130 using spacers 1140. The gap 1130 has a distance between one and ten microns ($1\mu$ to $10\mu$). Incident polarized light 1150 passes through the first plate 1110 and exits as refracted polarized light 1160 from the second plate 1120. A sample material 1170 (gas or liquid) passes within the gap 1130 between the plates 1110, 1120 to alter the degree of refraction:

Several types of glass compositions from known compositions to the glass composition can be used to produce the capillary tubes for 2DPB. The cell can be mounted in a spectroscopic ellipsometer. The material specimen to be studied can include organic solvents (liquid and vapor) that feature minimal optical absorption as the liquid or gas to be confined between the glass plates. The gas can be guided through the cell, with the region illuminated with the ellipsometer light source to monitor the changes in the polarization vector of the light upon refraction by the specimen. The process can be repeated with the wavelength of the incident light being changed from the infrared region up to the ultraviolet region. The data obtained can be analyzed using several dielectric models and to obtain information about the dielectric profile of the specimen. Preferably a dielectric profile gradient of the specimen can be established in the vicinity (within few nanometers) of the glass.

Characterization of the dielectric behavior of pure solvents can be followed by evaluation of mixtures, such as dry air or water vapor, using an automated gas mass flow mixer. Separation of the gases can be expected to occur near the surface of the glass plates. Changing the proportions of the mixed solvents may reverse the order of the separation next to the glass, thereby influencing the optical properties of the 2DPB. Solvents to study can include acetone, methanol, ethanol, isopropanol, and N,-N,-dimethyl-formamide both in liquid and vapor form.

Figure 12:
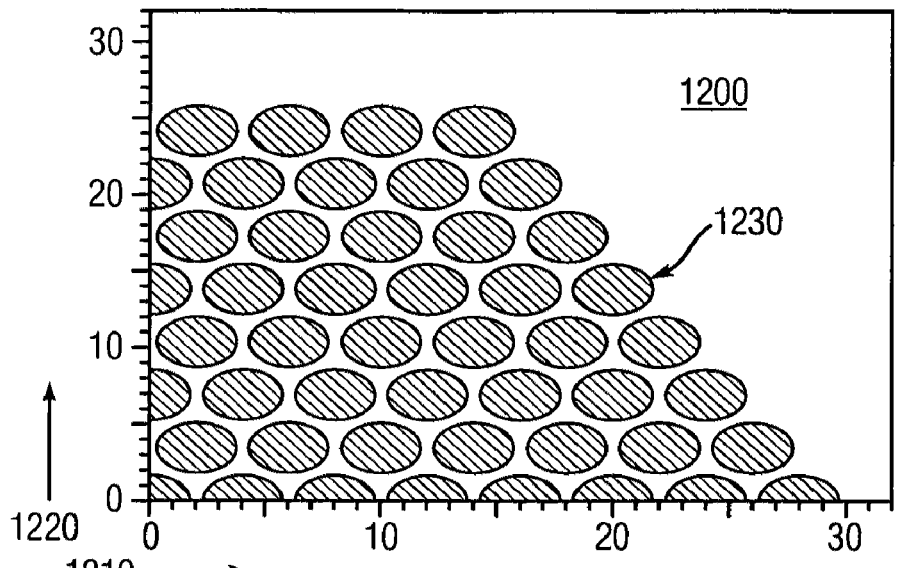
FIG. 12 is an elevation view of a computer-generated grid to calculate 2DPB optical properties.

FIG. 12 shows a computer generated grid 1200 that can be used to calculate the optical modes (bright dark pattern seen in SEM 600) of a 2DPB structure. The grid 1200 presents a two-dimensional scaled surface with abscissa 1210 and ordinate 1220, with round structures 1230 disposed in a hexagonal pattern. The effects of the defects and their potential ability of 2DPB structures as viable chemical sensor can thereby be investigated to determine the effects on defects of 2DPB produced by liquids and gases having established dielectric properties. The optical properties of chemically exposed 2DPB can be developed from these results through a theoretical model to predict the mode patterns of exposed 2DPB by using conventional tabulated optical data of generic chemicals.

Figure 13:
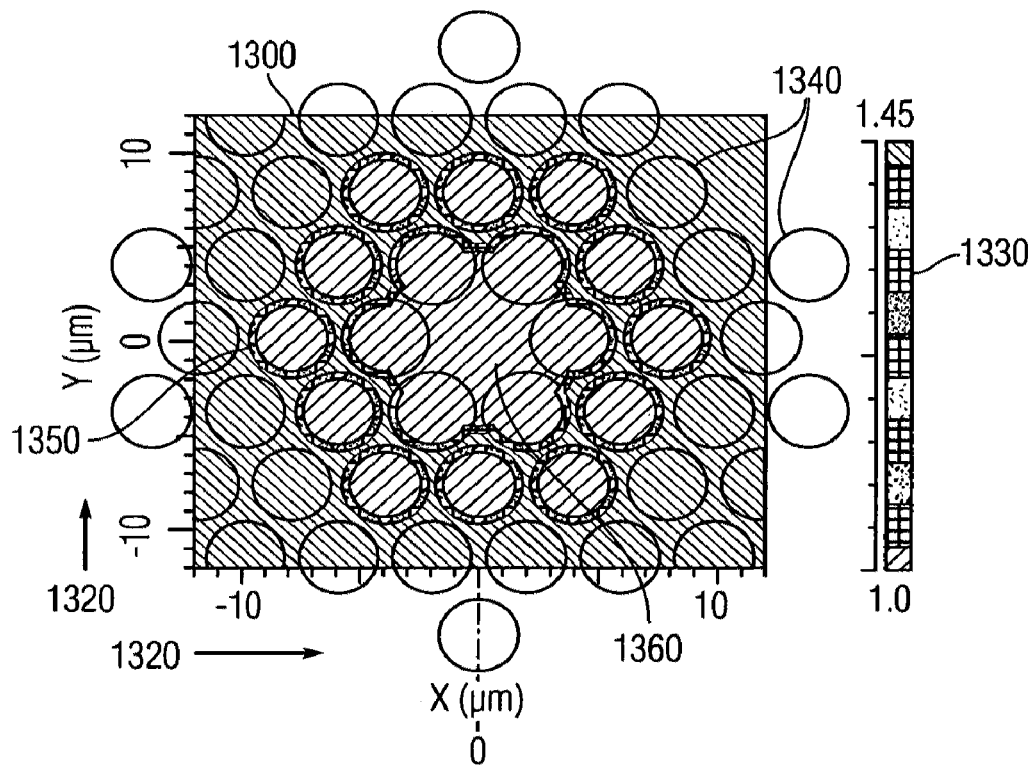
FIG. 13 is a contour plot for transverse index profile at Z=0.

FIG. 13 shows a computer generated index of refraction map 1300 on a two-dimensional scaled surface with abscissa 1310 and ordinate 1320. A legend 1330 denotes levels of index gradient. Within the background containing circle positions 1340 is a pattern of circular structures 1350 and a combinatorial hexagonal structure 1360. The index of refraction is the square-root of the dielectric constant. Maps such as these can be generated for the dielectric profiles from results of spectroscopic ellipsometry analysis of confined liquids and gases inside small spaces by establishing mode patterns based on the properties of the solvent at different volume fractions. Further, substances that absorb light in the region of interest can further be investigated to determine their change in optical properties of 2DPB, which are expected to be more drastic than for non-absorbing substances.

Figure 14:
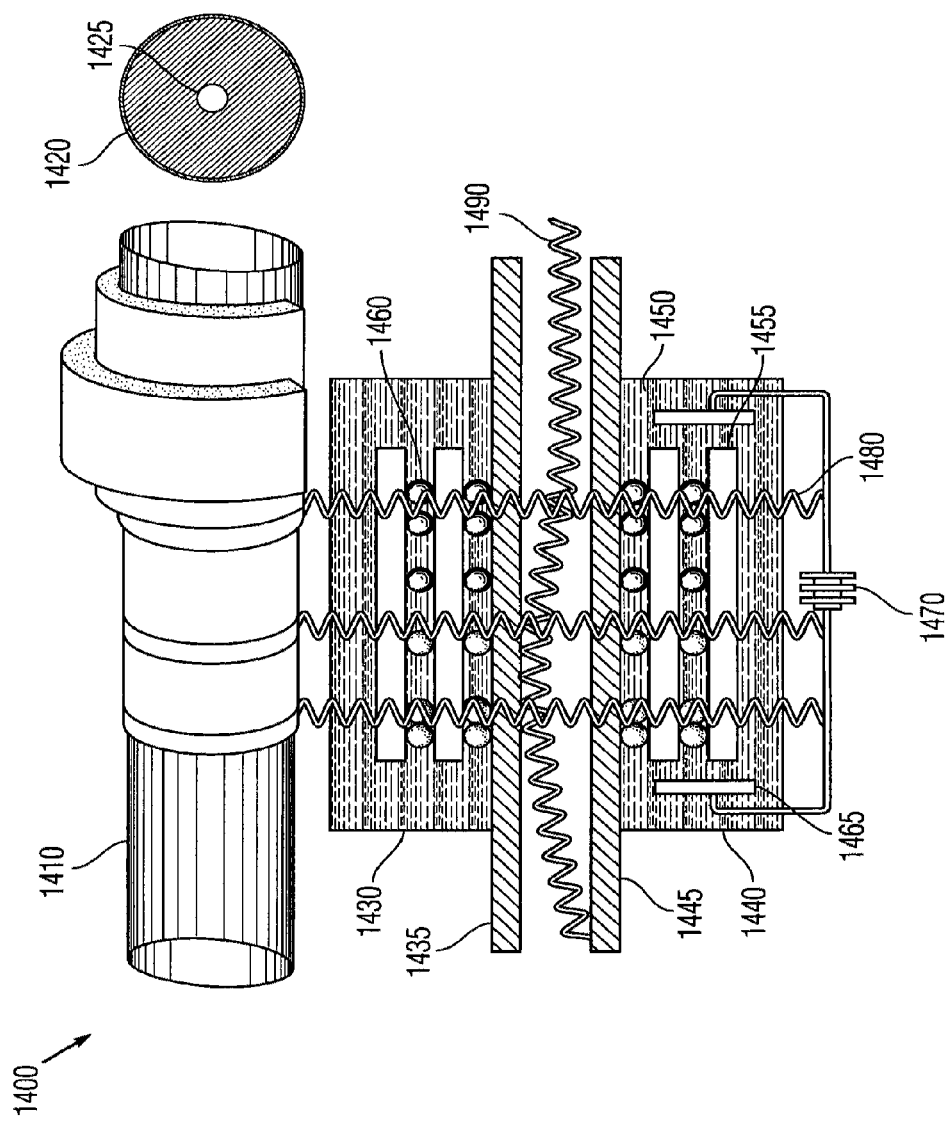
FIG. 14 is a block diagram view of a photonic crystal fiber with light escaping to form a dynamic barcode pattern, such as to identify potential chemical-biological agent.

FIG. 14 shows a diagram 1400 of an exemplary implementation for these techniques for a liquid sample. A fiber 1410 is disposed a cross-section 1420 with a center wave-guide core 1425. This can be analogized to a planar two-dimensional photonic crystal having a first cell 1430 disposed adjacent to a first cross-sectional plate 1435 and a second cell 1440 disposed adjacent to a second plate 1445, such that the first and second plates 1435, 1445 face each other to form a bounded wave-guide region analogous to the core 1425.

The cells 1430, 1440 can include a liquid medium 1450 as the sample within which are periodic arrays 1455 of capillary tubes with clusters of ions 1460 embedded therebetween. This is analogous to the fiber 1410 filled with the medium for such detection purposes. The second cell 1440 includes a circuit with electrodes 1465 powered by an electrical source 1470 to produce electromagnetic waves that emanate from the waveguide region both transverse mode 1480 and longitudinal mode 1490 between the plates 1435, 1445. This is analogous to the fiber having electrical potential across the ends.

The longitudinal mode 1490 represents light traveling longitudinally in the wave-guide region between the plates 1435, 1445, or by analogy through the core 1425 of the fiber 1410. The transverse mode 1480 that travels through the wave-guide plates 1435, 1445 reach the outer surface of their corresponding cells 1430, 1440 to emit a characteristic electromagnetic wave, such as light at a specific color to indicate presence of the medium. In this manner, the medium's presence can be indicated when immersed in an environment that unknowingly contains the medium 1450.

The concept can be applied alternatively without the center wave-guide core 1425 or analog plates 1435, 1445. A solid brick can be made from a two-dimensional photonic crystal (2DPC) filled with either a liquid or gas. This can be accomplished by shining light at the proper wavelength and a similar pattern forms at the opposite surface as the light escapes the photonic crystal. Light escaping the photonic crystal fiber forms a dynamic "barcode" pattern. The evolution of the barcode pattern can provide information to identify a potential CBW agent. Light escaping the photonic crystal fiber creates a type of dynamic barcode as further information to identify the CBW agent.

Figure 15:
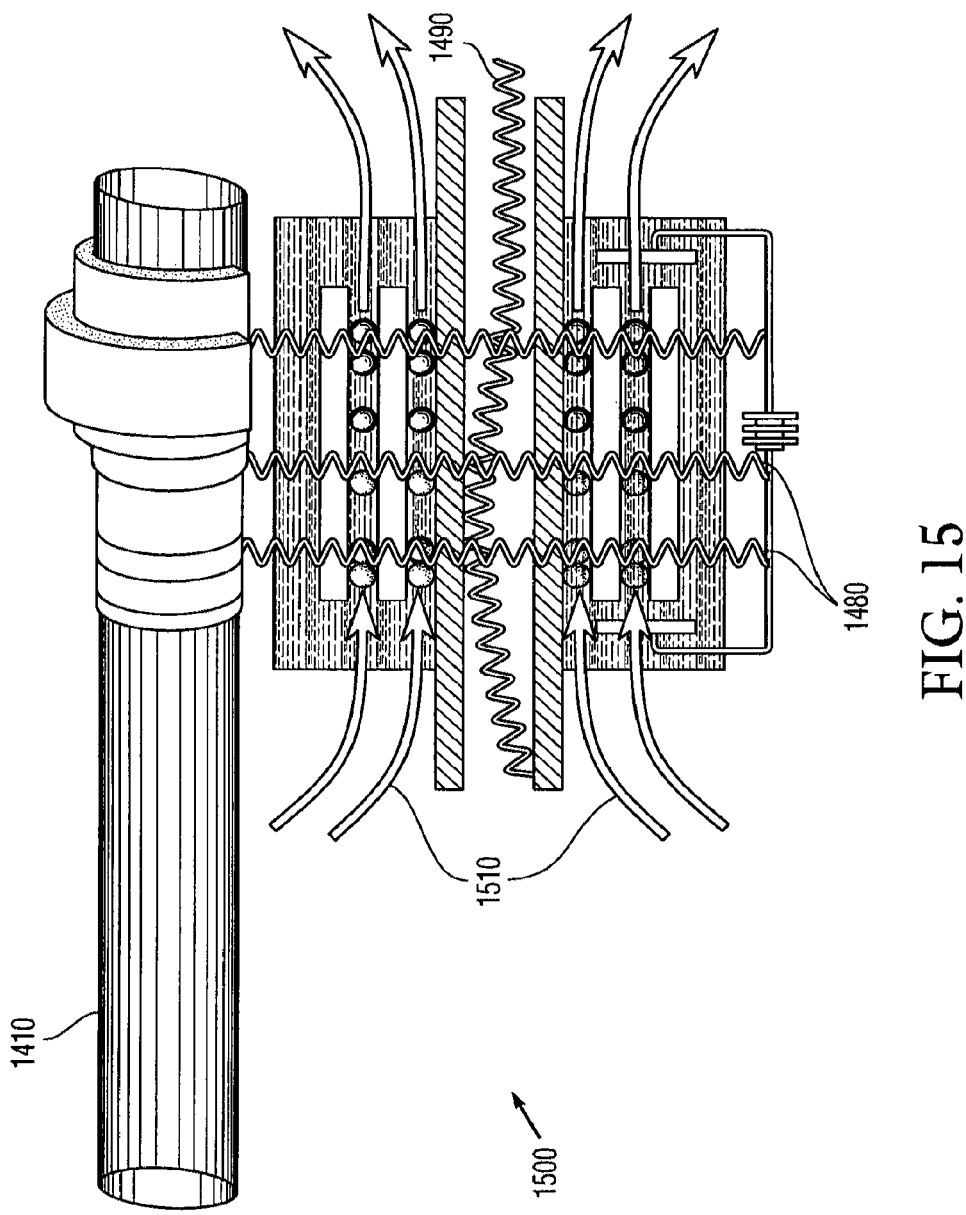
FIG. 15 is a diagram using gas instead of liquid sample.

FIG. 15 shows diagram 1500 for a gaseous flow mode instead of for a liquid sample. The fiber 1410 operates with gas 1510 passing between the periodic arrays 1455. The light that leaves the photonic fiber could be detected by digital video signal from a microscope optical path or by photo sensors integrated into the substrate hosting the photonic crystal fiber 1410. The analogous cells 1430, 1440 receive the gas 1510 and being energized produces waves in the transverse mode 1480 and longitudinal mode 1490.

The fraction of light leaving the fiber 1410 can be monitored by techniques known as optical frequency domain reflectometry (OFDR) and optical time domain reflectometry (OTDR). OFDR employs narrow pulses of optical radiation to probe the optical system under observation. The backscattered reflection is measured after each pule. The returned backscattered light can be used to determine scattering, reflection and absorption mechanisms in addition to other waveguide properties.

Some OFDR methods are capable of spatially resolving the places where the light escapes to within one millimeter. Another measurement method involves an optical effect using dispersion. Chromatic dispersion represents the complex relationship between the index or refraction and the wavelength of light. This relationship has an effect on the light-wave amplitude (due to the imaginary part of the index of refraction) and velocity (due to the real part of the index of refraction). Both amplitude and velocity change in relation to each other in accordance with the Kramer-Kronig relationship. Alight pulse that has a broad frequency component provides a change in pulse shape that can be quite pronounced and deterministic. Further, interferometry can be used as another method to characterize changes in light inside the photonic crystal fiber die to foreign matter inside the capillaries.

After the sample moves through the "optical characterization" zone, the sample moves to a sector surrounded by four electrodes forming a quadrupole configuration, which for its moment tensor represents a system of charges or masses. The quadrupole electrodes perform dipole relaxation time analysis (RTA), which uses alternating electric fields to rotate or "flip" molecules via interaction between the dipole field of the molecule and the external alternating field.

Each kind of molecule has a distinct dipole resonance due to the molecular mass and dipole moment. (Noble gases provide an exception to this as these that lack dipole and vary only in mass, but their inert chemical characteristics negate any potential hazard.) In addition, phase-selective, dipole-relaxation time analysis can be used to find information of the potential chiral properties of the sample.

Further, the sample can be moved to a sector where the physical dimension of the capillary tubes limits the dipole interaction to obtain a direct measurement of the molecular dimensions. Finally, the sample can be transferred to a sector where both absorption and emission spectroscopy are performed. At the end of one instance of observation, at least four physical properties of the sample can be issued, in which the information is used to identify the CBW agent. For additional information being needed, various exemplary embodiments can be implemented, as an array of several cascade systems such as described above, each optimized for a particular agent. Due to the small size of the device, as many as thousands of sensor systems can be implemented in an area of a few square inches.

The photonic band gap of photonic crystal fibers can be influenced by temperature changes and by morphological changes of the periodic array of capillary tubes. Consequently, alternative configurations of various embodiments could be used to develop microscopic thermometers and microscopic tension-compression gages. Torsional gages and balances represent another practical application. The inner surface of the fiber could be coated with molecules called "binders" that specifically bind CBW, TIC and other chemical and/or biological organisms or molecules. These binders are positioned (by electrophoresis or capillary motion) at specific coordinates along the long axis of the fiber. During the analysis, the sample mixture (e.g., chemical and/or biological compounds) is separated by electrophores, as described above.

As the compounds migrate along the fiber, specific analytes react with their cognate specific binder and be immobilized in that specific location (binder coordinates). After the entire sample has traversed the entire length of the fiber, the laser light can be sent along the fiber, and areas (coordinates) where an analyte-binder joint has developed, enables the light to escape. Escaping light from specified coordinate can be used to detect the presence on a specific chemical and/or biological compound. A variety of binders of plant, animal or synthetic origin are currently commercially available. Some binders that could be exploited are antibodies, lectins, short pieces of nucleic acids (commonly referred to as aptamers or oligomers), cavitands, carcerands, cage dextrin, zeolites, cryptophanes and memory polymers.

While certain features of the embodiments of the invention have been illustrated as described herein, many modifications, substitutions, changes and equivalents will now occur to those skilled in the art. It is, therefore, to be understood that the appended claims are intended to cover all such modifications and changes as fall within the true spirit of the embodiments.

What is claimed is:

1. A detector for indicating a material within a medium, said detector comprising:
    photonic waveguide comprising a plurality of fused capillary tubes surrounding a center core tube and having first and second opposite longitudinal ends, said plurality being disposed with periodic symmetry and exposed to the medium;
    first and second electrodes disposed between said ends of said waveguide;
    an electrical source for producing an electric field between said electrodes;
    an illumination source for emitting light into said core tube from said first opposite end, said light passing axially through said core tube and said plurality to produce an emission pattern;
    a photosensor for detecting said light that exhibits said emission pattern; and
    an analyzer for comparing said emission pattern transverse to said fiber against an established pattern for the material, and indicating match in response to correspondence between said patterns.

2. The detector according to claim 1, wherein said waveguide has a two-dimensional optical photonic band-gap.

3. The detector according to claim 1, wherein said analyzer monitors said emission pattern by optical frequency domain.

4. The detector according to claim 1, wherein said analyzer monitors said emission pattern by optical time domain reflectometry.

5. The detector according to claim 1, wherein said waveguide is an axisymmetric fiber.

6. The detector according to claim 5, wherein said fiber further comprises an annular sheath.

7. The detector according to claim 1, wherein said waveguide is a planar channel.

8. The detector according to claim 1, wherein said core tube and said plurality have distinguishable dielectric properties.

* * * * *